US011766232B2

(12) United States Patent
Hannemann et al.

(10) Patent No.: US 11,766,232 B2
(45) Date of Patent: Sep. 26, 2023

(54) METHOD, IMAGING APPARATUS AND COMPUTER PROGRAM PRODUCT FOR POSITIONING IMAGING-RELEVANT COMPONENTS

(71) Applicant: Siemens Healthcare GmbH, Erlangen (DE)

(72) Inventors: Thilo Hannemann, Erlangen (DE); Daniel Lerch, Weilersbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 127 days.

(21) Appl. No.: 17/376,217

(22) Filed: Jul. 15, 2021

(65) Prior Publication Data
US 2022/0030172 A1  Jan. 27, 2022

(30) Foreign Application Priority Data
Jul. 23, 2020  (DE) .................... 10 2020 209 323.7

(51) Int. Cl.
*A61B 6/00* (2006.01)
*A61B 5/00* (2006.01)
*A61B 5/055* (2006.01)

(52) U.S. Cl.
CPC ............... *A61B 6/547* (2013.01); *A61B 5/70* (2013.01); *A61B 5/055* (2013.01); *A61B 6/4441* (2013.01); *A61B 6/4464* (2013.01); *A61B 6/4476* (2013.01); *A61B 6/46* (2013.01); *A61B 6/488* (2013.01)

(58) Field of Classification Search
CPC ...... A61B 5/0077; A61B 6/0487; A61B 6/547
See application file for complete search history.

(56) References Cited

U.S. PATENT DOCUMENTS

| 2016/0113724 | A1 | 4/2016 | Stolka et al. |
| 2017/0322484 | A1 | 11/2017 | Erhard |
| 2019/0069871 | A1 | 3/2019 | Tkaczyk et al. |
| 2019/0139300 | A1 | 5/2019 | Kirchberg et al. |
| 2019/0318497 | A1* | 10/2019 | Zhao .................... A61B 6/0407 |

FOREIGN PATENT DOCUMENTS

DE       102017220500 A1    5/2019

* cited by examiner

*Primary Examiner* — Dani Fox
(74) *Attorney, Agent, or Firm* — Harness, Dickey & Pierce, P.L.C.

(57) ABSTRACT

A method is for positioning an imaging-relevant component of an imaging apparatus in an application-appropriate position for recording medical image data from a target region of a patient. In an embodiment, the method includes: acquiring information on the target region of the patient, acquiring a position of the patient relative to the imaging-relevant component, determining an application-appropriate position of the imaging-relevant component, determining a positioning instruction, and outputting the positioning instruction. An imaging apparatus of an embodiment includes an imaging-relevant component. The imaging-relevant component has a mechanical guide configured to position the imaging-relevant component along at least one degree of freedom of movement relative to a static arrangement of the imaging apparatus and/or a patient.

17 Claims, 4 Drawing Sheets

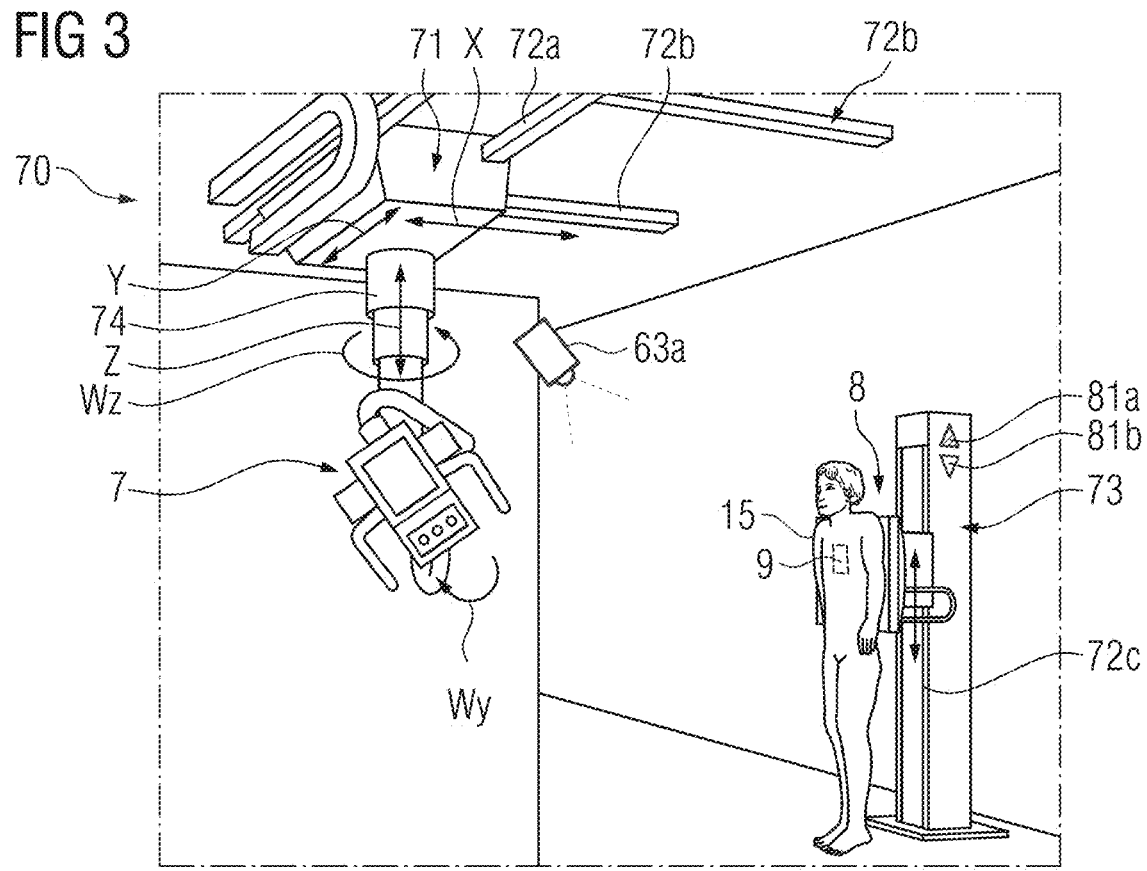

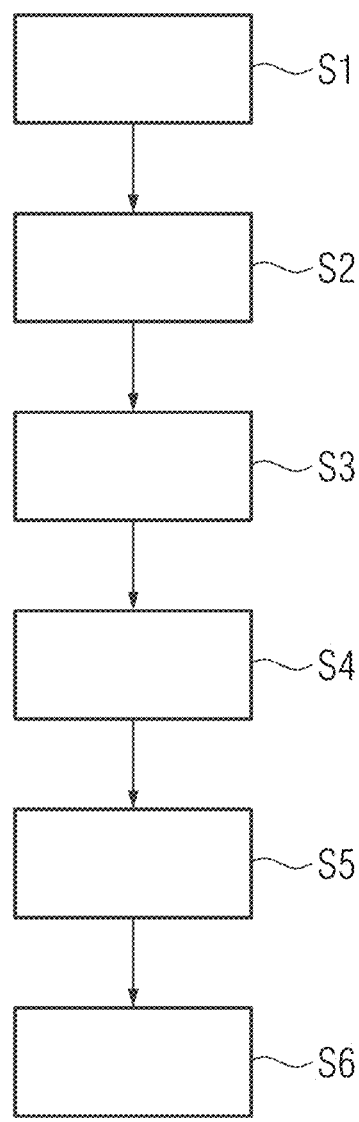

METHOD, IMAGING APPARATUS AND COMPUTER PROGRAM PRODUCT FOR POSITIONING IMAGING-RELEVANT COMPONENTS

PRIORITY STATEMENT

The present application hereby claims priority under 35 U.S.C. § 119 to German patent application number DE 102020209323.7 filed Jul. 23, 2020, the entire contents of which are hereby incorporated herein by reference.

FIELD

Example embodiments of the invention generally relate to a method for positioning an imaging-relevant component of an imaging apparatus in an application-appropriate position for recording medical image data from a target region of a patient, wherein the imaging-relevant component of the imaging apparatus is moved relative to a static arrangement of the imaging apparatus and/or the patient in order to achieve imaging coordinated with the target region of the patient. Example embodiments of the invention furthermore generally relate to a computer program product for executing a method according to the invention and an imaging apparatus according to the invention comprising an imaging-relevant component, wherein the imaging-relevant component has a mechanical guide configured to position the imaging-relevant component along at least one degree of freedom of movement relative to a static arrangement of the imaging apparatus and/or a patient.

BACKGROUND

Medical imaging methods typically require exact positioning of a diagnostically relevant body region of a patient relative to the imaging apparatus used. Herein, typical imaging apparatuses, such as, for example, magnetic resonance apparatuses, computed tomography apparatuses, fluoroscopy apparatuses or X-ray apparatuses have an imaging region in which the body region of the patient to be examined is positioned. The imaging region can, for example, be positioned at a predetermined position of the imaging apparatus, such as, for example, an isocenter of a magnetic resonance apparatus or can be moved via an emitter/detector arrangement, such as, for example, on a C-arm of an X-ray apparatus, relative to the imaging apparatus and/or the patient.

Herein, the positioning of the patient relative to the imaging region can have a great influence on the quality of the image data recorded. In one example, changing an angle of an X-ray source of an X-ray apparatus by a few degrees can result in a two-dimensional projection of a joint cavity being superimposed with other anatomical structures and becoming unusable for diagnosis. In another example, a radiation cone of an X-ray tube that is faded in slightly too far can mask an anatomical structure from the two-dimensional projection as the result of which a pathological change to the tissue can be overlooked. Correct positioning of the patient relative to the imaging region is equally important with all imaging apparatuses in order to enable high-quality image data and hence high-quality diagnosis. Repetition of imaging due to incorrect positioning is often difficult in clinical practice since the number of patients is usually high and the imaging apparatuses are accordingly used to capacity. In addition, in particular X-ray-based imaging methods are associated with the application of ionizing radiation to which the patient should not be exposed unnecessarily or repeatedly.

Nowadays, fully automatic solutions are available for ensuring high accuracy of the positioning of the patient relative to an imaging region of the imaging apparatus. These enable independent positioning of imaging-relevant components, such as, for example, a patient table or an emitter/detector arrangement in order to achieve correct positioning of a diagnostically relevant target region of the patient in the imaging region of the imaging apparatus.

SUMMARY

The inventors have discovered that fully automated solutions often entail high costs due to the motorized subcomponents and are not available to a large number of end customers, such as, for example, small and medium-sized radiological practices. Such small and medium-sized radiological practices often lack the trained staff required to ensure reproducible quality with manual positioning of the patient and/or the imaging-relevant components taking account of the diagnostically relevant issue in respect of the individual patient.

At least one embodiment of the present invention provides a method, an apparatus and a computer program product, which increases the quality of patient positioning relative to an imaging apparatus and avoids the high costs associated with fully-automated positioning of imaging-relevant components.

Advantageous embodiments and expedient developments are the subject matter of the claims.

With the method according to at least one embodiment of the invention for positioning an imaging-relevant component of an imaging apparatus in an application-appropriate position for recording medical image data from a target region of a patient, the imaging-relevant component of the imaging apparatus is moved relative to a static arrangement of the imaging apparatus and/or the patient in order to achieve imaging coordinated with the target region of the patient. An imaging apparatus preferably constitutes a medical device suitable for performing an imaging method for acquiring image data and/or for recording any spatially-resolved measured values of a tissue of the patient. Examples of imaging apparatuses constitute magnetic resonance apparatuses, computed tomography apparatuses, positron emission tomography apparatuses, single photon emission computed tomography apparatuses, but also X-ray apparatuses, such as C-arms, gamma cameras, mammography apparatuses and Bucky wall stands.

The imaging apparatus according to at least one embodiment of the invention comprises an imaging-relevant component, at least one sensor, a computing unit and an output interface, wherein the imaging-relevant component has a mechanical guide configured to position the imaging-relevant component along at least one degree of freedom of movement relative to a static arrangement of the imaging apparatus and/or a patient. The imaging-relevant component can be embodied according to one of the above-described embodiments. A mechanical guide of the imaging-relevant component can have any mechanism embodied to move the imaging-relevant component relative to the static arrangement of the imaging apparatus. The mechanical guide can, for example, comprise a rail system, a trolley, a telescope system, a joint or the like that enables guidance of the imaging-relevant component along a predetermined movement trajectory or predetermined degree of freedom of movement. Herein, the degree of freedom of movement can, for example, constitute a pivot point and/or a path along which the imaging-relevant component can be moved and/or is mounted such that it can move. It is conceivable that the imaging-relevant component has a plurality of degrees of freedom of movement, such as, for example, two, three, four or more degrees of freedom. It is equally conceivable that the mechanical guide has a pivot joint or a ball joint that enables substantially three-dimensional movement of the imaging-relevant component in a limited range of motion.

The computer program product according to at least one embodiment of the invention can be loaded into a memory of the computing unit of the imaging apparatus and has program code in order to execute a method according to at least one embodiment of the invention when the computer program product is executed in the computing unit of the imaging apparatus.

A method, according to at least one embodiment of the invention, is for positioning an imaging-relevant component of an imaging apparatus in an application-appropriate position for recording medical image data from a target region of a patient, the imaging-relevant component of the imaging apparatus being movable relative to at least one of a static arrangement of the imaging apparatus and the patient, to achieve imaging coordinated with the target region of the patient, the method comprising:

acquiring information on the target region of the patient;

acquiring a position of the patient relative to the imaging-relevant component;

determining an application-appropriate position of the imaging-relevant component in dependence of the information acquired on the target region of the patient;

determining a positioning instruction in dependence of the position of the patient aquired relative to the imaging-relevant component, and the application-appropriate position of the imaging-relevant component determined; and outputting the positioning instruction.

An imaging apparatus, according to at least one embodiment of the invention, comprises:

an imaging-relevant component including a mechanical guide configured to position an imaging-relevant component along at least one degree of freedom of movement relative to at least one of a static arrangement of the imaging apparatus and a patient;

at least one sensor embodied to acquire a position of a target region of the patient relative to the imaging-relevant component;

at least one processor embodied to determine the application-appropriate position of the imaging-relevant component and to derive a positioning instruction at least in dependence on the position of the patient relative to the imaging-relevant component; and an output interface configured to output the positioning instruction.

BRIEF DESCRIPTION OF THE DRAWINGS

Further advantages and details of the present invention may be derived from the example embodiments described below and with reference to the drawings, in which:

FIG. 3 shows an embodiment of an imaging apparatus according to the invention,

FIG. 4 shows a possible flow diagram of a method according to an embodiment of the invention.

DETAILED DESCRIPTION OF THE EXAMPLE EMBODIMENTS

Figure 1:
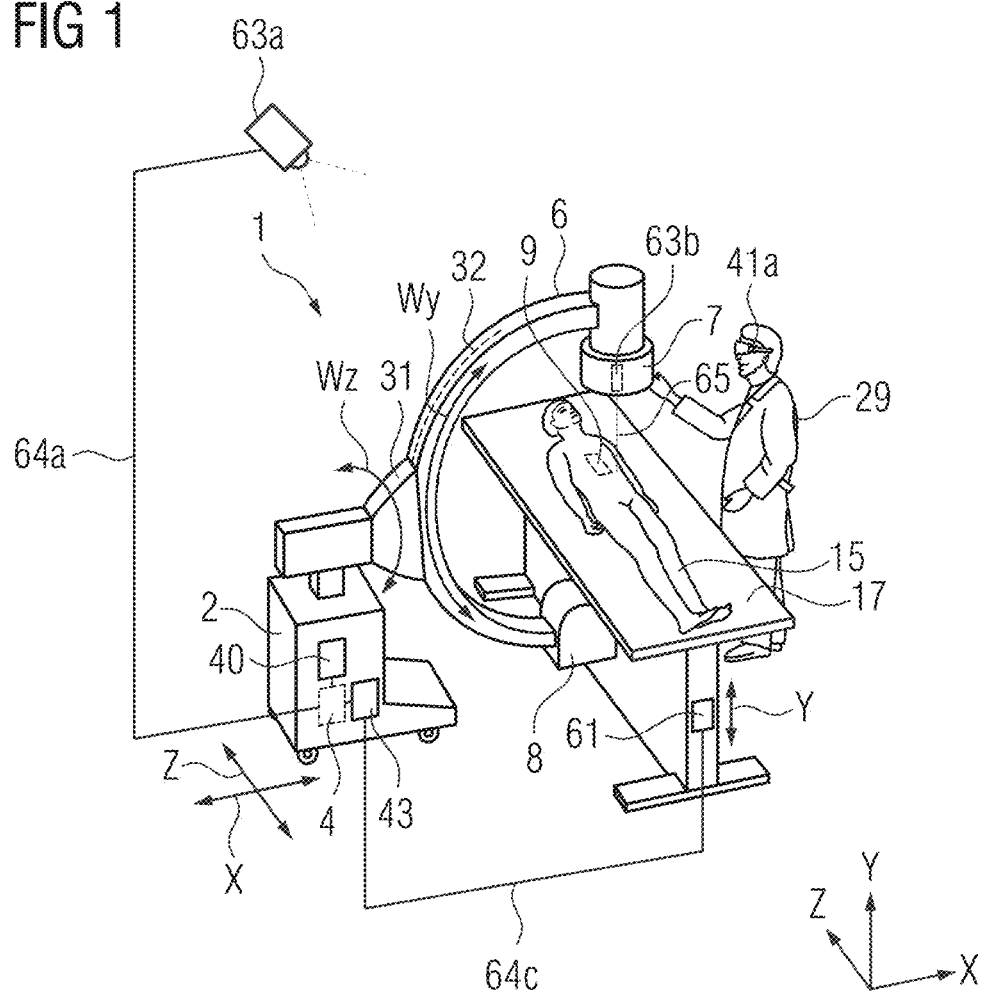
FIG. 1 shows an embodiment of an imaging apparatus according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments.

Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

With the method according to at least one embodiment of the invention for positioning an imaging-relevant component of an imaging apparatus in an application-appropriate position for recording medical image data from a target region of a patient, the imaging-relevant component of the imaging apparatus is moved relative to a static arrangement of the imaging apparatus and/or the patient in order to achieve imaging coordinated with the target region of the patient. An imaging apparatus preferably constitutes a medical device suitable for performing an imaging method for acquiring image data and/or for recording any spatially-resolved measured values of a tissue of the patient. Examples of imaging apparatuses constitute magnetic resonance apparatuses, computed tomography apparatuses, positron emission tomography apparatuses, single photon emission computed tomography apparatuses, but also X-ray apparatuses, such as C-arms, gamma cameras, mammography apparatuses and Bucky wall stands.

Herein, an imaging-relevant component of the imaging apparatus can be any component or an arrangement of components of the imaging apparatus. The imaging-relevant component preferably serves the purpose of coordinating a diagnostically relevant target region of the patient with an imaging region of the imaging apparatus in order to enable recording of medical image data from the target region of the patient. Possible examples of imaging-relevant components include a patient table of a computed tomography apparatus, an emitter/detector arrangement of a C-arm or a Bucky wall stand and a receiving table or compression paddle of a mammography apparatus. A position and/or alignment of the imaging-relevant component can preferably be moved relative to a substantially static arrangement of the imaging apparatus and/or the patient in order to enable imaging coordinated with the target region of the patient.

Herein, the imaging-relevant component of the imaging apparatus is in particular positioned in an application-appropriate position. An application-appropriate position can constitute a spatial location and/or an orientation of the imaging-relevant component in which the target region of the patient is coordinated with the imaging region of the imaging apparatus. Hence, the positioning of the imaging-relevant component in the application-appropriate position can enable recording of image data from the target region of the patient. This can mean that the image data reproduces a volume and/or projection of the target region of the patient in a desired manner. However, it can equally mean that a spatial resolution and/or contrast of the image data is coordinated with a diagnostic issue or indication relating to the target region. Herein, a target region can constitute any body region of the patient, such as, for example, an arm, leg, head, shoulder, hip or the like. It is in particular conceivable that the target region, such as, for example, an organ or a section of a skeleton, is located within the patient's body. The method according to the invention has the following steps.

In one step of the method according to at least one embodiment of the invention, information on the target region of a patient is acquired. Information on the target region of the patient can, for example, comprise a name of the target region, a description of the location of the target region and/or a medical diagnosis that enables the location of the target region in and/or on the patient to be identified. It is conceivable that the information on the target region of the patient is retrieved from a radiology information system (RIS) and/or a hospital information system (HIS) or is entered by a user of the imaging apparatus via a suitable input interface or operator control unit of the imaging apparatus. It is furthermore conceivable that, during the acquisition of the information on the target region of the patient, patient information, such as, for example, age, gender, height, weight and/or medical history and information on the type of examination, such as, for example, imaging of the patient's shoulder, head, hip or tumor is also read in. In addition, the acquisition of the information on the target region of the patient can also comprise the acquisition of information on a position, alignment and/or structure of the imaging-relevant component. The information on the position and/or alignment of the imaging-relevant component can, for example, constitute a preferred position of the target region relative to the imaging region of the imaging apparatus and a preferred angle and/or distance of an X-ray source with respect to the respective target region of the patient.

In a further step of the method according to at least one embodiment of the invention, a position of the patient relative to the imaging-relevant component is acquired. A relative position can, for example, be a distance between a point on a surface of the target region of the patient and a point on a surface of the imaging-relevant component. It is equally conceivable that the relative position represents a distance between a centroid of the target region of the patient and any point on the surface of the imaging-relevant component. The relative position can furthermore also be a mean distance between the surface of the patient and the surface of the imaging-relevant component. It is further conceivable that the relative position is characterized by a volume of an interspace between the patient and the imaging-relevant components.

The acquisition of the position of the patient relative to the imaging-relevant component is preferably performed via at least one sensor. In one embodiment, the sensor can be a distance sensor that measures the distance between the target region of the patient and the imaging-relevant component. The distance sensor can, for example, be embodied as an ultrasonic measuring device, a laser measuring device, a LiDAR measuring device or the like. However, it is equally conceivable that the sensor is embodied as a camera, such as, for example, a 3D camera, a 2D camera and/or an infrared camera. The camera preferably records two-dimensional and/or three-dimensional image information on the patient and/or the target region of the patient. The sensor can furthermore be embodied as an incremental encoder to detect a change in position of the imaging-relevant component. Such a change in position of the imaging-relevant component can constitute a change in location and/or a change in angle, such as, for example, a vertical displacement, a horizontal displacement, a tilt and/or a rotation of the patient table on which the patient is positioned. The incremental encoder can, for example, have a sliding contact, photoelectric scanning, magnetic scanning, interference scanning and/or a toothed-wheel encoder or the like. The imaging apparatus can in particular comprise a plurality of sensors, which in turn have a plurality of different sensor technologies, such as, for example, cameras, distance sensors and/or incremental encoders.

The signals from the sensors, in particular the image data from cameras, can be transmitted to a computing unit of the imaging apparatus via a signal connection in order to determine the position of the patient relative to the imaging-relevant component. The image data of the patient and the imaging-relevant component are preferably used to create a three-dimensional map of an examination room in which the patient and the imaging-relevant component are located. The three-dimensional map may be used to determine distances between any points on a surface of the patient and a surface of the imaging-relevant component. It is furthermore conceivable that the patient and/or the imaging-relevant component have reference points that facilitate a determination of the distance between the patient and/or the imaging-relevant component. Such reference points can constitute both natural orientation points, such as, for example, a nose, eye or shoulder of the patient, but also artificial orientation points, such as, for example, reflective or luminous markers on the imaging-relevant component and/or the patient.

In a further step of the method according to at least one embodiment of the invention, an application-appropriate position of the imaging-relevant component is determined in dependence on the information on the target region of the patient. Herein, the application-appropriate position can, for example, be read in from a database in which information on application-appropriate positions of the imaging-relevant component for a plurality of target regions of the patient is stored. However, it is equally conceivable that the determination of the application-appropriate position of the imaging-relevant component is performed in dependence on a body model with which the location of the target regions of the patient can be ascertained with a statistical probability. The determination of the application-appropriate position of the imaging-relevant component can further also be performed by way of the use of intelligent algorithms, for example in dependence on patient information and/or medical image data from a database. The determination of the application-appropriate position of the imaging-relevant component preferably comprises a determination of coordinates or location information that spatially define the application-appropriate position of the imaging-relevant component for the recording of image data from the target region of the patient. In one example, the coordinates or location information can comprise a position and/or an orientation of a patient table, X-ray detector or a gamma camera.

According to a further step of the method according to at least one embodiment of the invention, a positioning instruction is determined in dependence on the position of the patient relative to the imaging-relevant component and the application-appropriate position of the imaging-relevant component. In a simple example, a positioning instruction can constitute a bit, such as, for example, a "zero" or a "one". Herein, the "zero" can encode a backward movement, while the "one" encodes a forward movement and vice versa. A patient table, a recording table, a compression paddle or the like can be moved in dependence on such a positioning instruction along a spatial direction, such as, for example, along a horizontal line or a vertical line, into the application-appropriate position. However, the positioning instruction can also comprise coordinates and/or location information on the imaging-relevant component that spatially define the application-appropriate position of the imaging-relevant component. In one preferred embodiment, the positioning instruction has three-dimensional coordinates of the application-appropriate position of the imaging-relevant component. The positioning instruction can further also comprise additional information, such as, for example, a difference between the current position of the imaging-relevant component and the application-appropriate position of the imaging-relevant component and information on the achievement of the application-appropriate position or the like.

In a further step of the method according to at least one embodiment of the invention, the positioning instruction is output. The outputting of the positioning instruction can, for example, be performed via an analog or digital signal via an appropriately configured electrical signal connection or a wireless signal connection. During the outputting, the positioning instruction is preferably visualized on a display unit and displayed to a user of the imaging apparatus. Herein, the output can comprise any information from the positioning instruction. In a simple example, the output can be a bit that triggers the illumination of an arrow-shaped first indication element pointing in the direction of the application-appropriate position of the imaging-relevant component. The first indication element can be illuminated via a light source until the application-appropriate position of the patient table is achieved. The patient table can also have a second arrow-shaped indication element aligned in the opposite direction to the first indication element and which lights up in dependence on the output if the application-appropriate position of the imaging-relevant component has been exceeded and movement in the opposite direction is required.

In a further example, the output can comprise a two-dimensional or three-dimensional map of the examination room in which the current position of the patient and the current position of the imaging-relevant component and the application-appropriate position of the imaging-relevant component are superimposed.

The output of the positioning signal can comprise the output of a control signal. The control signal can, for example, be used to actuate a motor apparatus and/or a braking apparatus which can influence a movement and/or position of the imaging-relevant component. Preferably, at least one part of the positioning instruction is output via a display unit directly to a user of the imaging apparatus who is thereby enabled to position the imaging-relevant component in the application-appropriate position. A display unit constitutes, for example, a monitor, a projection screen, VR glasses, a smartwatch, an illuminated indication element or the like. It is conceivable that the positioning instruction is updated continuously or at discrete time intervals on the display unit in order to output a current status of positioning to the user of the imaging apparatus.

In a further step of the method according to at least one embodiment of the invention, the imaging-relevant component is positioned in the application-appropriate position in dependence on the positioning instruction. The positioning can, for example, be performed by way of the displacement, rotation and/or tilting of the imaging-relevant component by the user of the imaging apparatus. For this purpose, the imaging-relevant component can, for example, be connected to a rail system or a telescope system and/or have a pivot joint, a ball joint, a hinge, a multiple joint or the like that enable movement along one or more degrees of freedom of movement. The positioning of the imaging-relevant component along the possible degrees of freedom of movement is preferably performed by the user of the imaging apparatus. The user can position the imaging-relevant component in dependence on the positioning instruction output on the display unit.

It is furthermore conceivable that the positioning of the imaging-relevant component is assisted via a motor element and/or a braking apparatus. Assistance can, for example, comprise the correction of minor positioning errors of the imaging component via a motor element or the limiting of the movement of the imaging-relevant component by the braking apparatus. Herein, the motor element and/or the braking apparatus can be actuated via the control signal of the positioning instruction. Preferably, a time of actuation of the motor element and/or the braking apparatus is correlated with a current position, a current speed or a difference between the current position and the application-appropriate position of the imaging-relevant component and further information, such as, for example, the weight of the imaging-relevant component and/or the weight of the patient. Such information can, for example, be ascertained from the patient information or acquired via the at least one sensor.

The method according to at least one embodiment of the invention advantageously enables accurate positioning of the imaging-relevant component while at the same time avoiding high-cost motorization for fully automatic positioning of the imaging-relevant component. The output of the positioning instruction on the display unit further advantageously enables the user of the imaging apparatus to be informed of the current status of the positioning so that the user can adapt the position of the imaging-relevant component according to the positioning instruction.

In one possible embodiment of the method according to at least one embodiment of the invention, the determination of the application-appropriate position of the imaging-relevant component is performed by way of intelligent algorithms and/or via a body model. An intelligent algorithm can mean any application of artificial intelligence. Artificial intelligence can, for example, comprise a self-learning algorithm, a neural network, an expert system or the like, which determine the application-appropriate position in dependence on patient information and further data, in particular image data from a plurality of patients. In one example a neural network can be trained to determine the application-appropriate position of the imaging-relevant component in dependence on a target region of the patient with data from other patients from a database. It is equally conceivable that the data from the database is linked to comments by a medical professional or a user of the imaging apparatus comprising a statement on the quality of the respective positioning of the imaging-relevant component. Such a comment can be used by the intelligent algorithm as a boundary condition or input variable R in order to determine the application-appropriate position of the imaging-relevant component. On the other hand, an expert system can, for example, determine the application-appropriate position of the imaging-relevant component based on a known geometric arrangement of the imaging apparatus, a known degree of freedom of movement of the imaging-relevant component, but also patient information and/or the target region of the patient. It is equally conceivable that the expert system makes use of measurement data from the at least one sensor and/or a body model in order to determine the application-appropriate position of the imaging-relevant component. The body model preferably provides a virtual map of a human patient which can be adapted to an individual patient in dependence on the patient information. It is equally conceivable that positions of target regions, in particular various organs, are already contained in the body model. The expert system can further be embodied to localize the target region of the patient in the three-dimensional map of the examination room and to determine an application-appropriate position of the imaging-relevant component.

The use of intelligent algorithms and/or the body model enables the application-appropriate position of the imaging-relevant component to be determined in a short time and reproducibly in dependence on a plurality of influencing factors. This can advantageously reduce the duration of the performance of the imaging for recording image data from the target region of the patient.

In one preferred embodiment of the method according to the invention, the positioning of the imaging-relevant component in the application-appropriate position is performed manually in dependence on the positioning instruction. Manual positioning of the imaging-relevant component can mean that the imaging-relevant component is moved by the user of the imaging apparatus along the corresponding degrees of freedom of movement into the application-appropriate position. In a simple example, the patient table of a magnetic resonance apparatus is moved by the user together with the patient on a rail system or a trolley along a horizontal line into the application-appropriate position so that the target region of the patient is positioned in the isocenter of the magnetic resonance apparatus. Herein, the user of the magnetic resonance apparatus is guided by the positioning instruction, which is output to the user, for example via the display unit and/or the indication element on the magnetic resonance apparatus and/or the patient table.

Manual positioning of the imaging-relevant component advantageously enables costly motorization of the imaging-relevant component for fully automated setting of the application-appropriate position to be avoided. This advantageously enables manufacturing costs and operating costs for the imaging apparatus to be reduced. Furthermore, the use of artificial intelligence and/or the body models to determine the application-appropriate position of the imaging-relevant component can advantageously be combined with manual performance of the positioning thus enabling highly accurate positioning to be achieved in a short time.

According to one possible embodiment of the method according to the invention, the outputting of the positioning instruction comprises outputting an optical signal and/or an acoustic signal and/or force feedback. An optical signal can, for example, comprise the illumination of a light source, but also a visual depiction of an indication, such as, for example, a text field, a geometric object, a numerical digit, a virtual map of the examination room and/or the patient and/or the imaging-relevant component and any combinations of such indications, on a display unit. In one preferred embodiment, the optical signal of the positioning instruction comprises a three-dimensional map of the examination room with the imaging-relevant component and the patient in which the application-appropriate position of the imaging-relevant component is, for example, mapped as a semi-transparent or dashed schematic drawing. As described above, the three-dimensional map of the examination room can be acquired via a 3D camera and updated continuously or at discrete time intervals. The three-dimensional map of the examination room can, for example, be output to the user of the imaging apparatus via a monitor, a projection screen and/or VR glasses (virtual reality glasses). In one embodiment, the application-appropriate position of the imaging-relevant component is output to the user via VR glasses with a transparent viewing lens. Herein, it is possible to dispense with an output of the three-dimensional examination room since the user can view the examination room with the patient, the imaging apparatus and the imaging-relevant component through the transparent viewing lens of the VR glasses. With this embodiment, the positioning instruction is preferably faded in or projected onto the viewing lens of the VR glasses for the user as a semi-transparent or dashed schematic drawing so that the user can move the imaging-relevant component into the application-appropriate position in dependence on the positioning instruction.

However, the positioning instruction can also comprise an acoustic signal and/or force feedback, such as, for example, a tone or a vibration, whose intensity, duration and/or frequency change as the distance of the imaging-relevant component from the application-appropriate position increases or decreases. In a simple example, the compression paddle of a mammography apparatus is guided into the application-appropriate position on a patient's breast.

Herein, the user of the mammography apparatus can be informed of the achievement of the application-appropriate position of the compression paddle by way of the vibration of a mobile device, such as, for example, a smartwatch or a remote control of the compression paddle in that the vibration frequency of the mobile device changes as the compression paddle approaches the application-appropriate position. The vibration can also be adapted by way of a variable duration of pauses between individual vibration pulses, wherein, for example, the duration of the pauses between the vibration pulses decreases as the distance between the current position of the imaging-relevant component and the application-appropriate position decreases. When the application-appropriate position is achieved, it is, for example, possible for a sustained vibration pulse to be output in order to inform the user accordingly.

Outputting the optical and/or acoustic signal and/or force feedback enables the user of the imaging apparatus to be directly informed of the current status of the positioning of the imaging-relevant component. Furthermore, when the force feedback, the acoustic signal and/or the optical signal are output via VR glasses, the positioning instruction is positioned directly on the user and/or in the user's field of view so that it is advantageously possible to avoid cumbersome tracking of the positioning instruction on a separately installed display unit.

In one possible embodiment of the method according to the invention, the outputting of the positioning instruction comprises outputting a control signal, wherein, during the positioning of the imaging-relevant component, the imaging-relevant component is locked in the application-appropriate position via a braking apparatus, wherein the braking apparatus is transferred to a locking position by way of the control signal. The control signal can, for example, be transmitted to the braking apparatus as an analog or digital signal via an electrical signal connection. The transmission of the control signal is preferably synchronized with the movement of the imaging-relevant component such that the imaging-relevant component is locked in the application-appropriate position by way of a force exerted by the braking apparatus. It is conceivable that the computing unit of the imaging apparatus is embodied to determine a position, speed, weight, push force or the like of the imaging-relevant components in dependence on data from the at least one sensor and/or patient information in order to synchronize the output of the control signal to the braking apparatus with the movement of the imaging-relevant component. In one possible embodiment, the computing unit determines the current kinetic energy of the imaging-relevant component in dependence on the weight and speed of the imaging-relevant component. The current kinetic energy can be used to ascertain a braking force that has to be applied in order to lock the imaging-relevant component in the application-appropriate position. Herein, it is conceivable that a braking effect of the braking apparatus is varied via the control signal. Furthermore, at least one sensor of the imaging apparatus can also be embodied as an incremental encoder or an absolute encoder which directly acquires a current position of the imaging-relevant component and transfers it to the computing unit. The computing unit can then determine a position and/or speed of the imaging-relevant component and take this into account during the determination of the positioning instruction. In a further embodiment, the braking apparatus can have a stop element that limits the movement of the imaging-relevant component along one or more degrees of freedom of movement upon contact with the imaging-relevant component. It is conceivable that a position of the stop element and/or the braking apparatus is set along a degree of freedom of movement of the imaging-relevant component in dependence on the positioning instruction.

The actuation of the braking apparatus in dependence on the positioning instruction advantageously enables a costly motor for positioning the imaging-relevant component to be avoided. This enables manufacturing costs and operating costs to be reduced compared to a fully automated imaging apparatus. The provision of the braking apparatus further also enables accurate positioning of the imaging-relevant component to be carried out by fewer qualified staff since locking in the application-appropriate position can advantageously be performed by the braking apparatus.

In one possible embodiment of the method according to the invention, a minor positioning error during the positioning of the imaging-relevant component in the application-appropriate position is corrected via a motor element, wherein, during the correction of the minor positioning error, the motor element moves the imaging-relevant component into the application-appropriate position on the patient in dependence on the positioning instruction. Herein, a minor positioning error can constitute a minor difference between the current position of the imaging-relevant component and the application-appropriate position of the imaging-relevant component. The motor element is preferably embodied to carry out fine adjustment of the position of the imaging-relevant component in an order of magnitude corresponding to the minor positioning error. This can mean that the motor element can position the imaging-relevant component along a limited path distance, for example a path distance of a few millimeters or a few centimeters in order to correct the minor positioning error of the imaging-relevant component. It can equally mean that the minor positioning error can be corrected by the motor element in a limited time interval, for example within a few milliseconds to a few seconds. In one possible embodiment, the manual positioning of the imaging-relevant component by the user is completed as soon as the minor positioning error of the imaging-relevant component is within the limited path distance of the motor element and/or can be corrected by the motor element within the limited time interval.

The fine adjustment of the position of the imaging-relevant component can, for example, be performed by actuating the motor element with a control signal of the positioning instruction. Such a control signal can be transmitted to the motor element as an analog or digital signal from the computing unit and/or control unit of the imaging apparatus via a suitable signal connection. It is conceivable that a single motor element enables the correction of minor positioning errors along several degrees of freedom of movement of the imaging-relevant component. However, the imaging apparatus can equally have a plurality of motor elements which correct minor positioning errors along several degrees of freedom of movement in dependence on the control signal of the positioning instruction.

The use of motor elements that correct minor positioning errors of the imaging-relevant component in dependence on the positioning instruction advantageously enables costly motor elements for fully automated positioning of the imaging-relevant component along the path of movement of the imaging-relevant component to be avoided. This enables manufacturing costs and operating costs to be reduced compared to a fully automated imaging apparatus, wherein it is advantageously possible to ensure a comparable quality of the positioning of the imaging-relevant component.

The imaging apparatus according to at least one embodiment of the invention comprises an imaging-relevant component, at least one sensor, a computing unit and an output interface, wherein the imaging-relevant component has a mechanical guide configured to position the imaging-relevant component along at least one degree of freedom of movement relative to a static arrangement of the imaging apparatus and/or a patient. The imaging-relevant component can be embodied according to one of the above-described embodiments. A mechanical guide of the imaging-relevant component can have any mechanism embodied to move the imaging-relevant component relative to the static arrangement of the imaging apparatus. The mechanical guide can, for example, comprise a rail system, a trolley, a telescope system, a joint or the like that enables guidance of the imaging-relevant component along a predetermined movement trajectory or predetermined degree of freedom of movement. Herein, the degree of freedom of movement can, for example, constitute a pivot point and/or a path along which the imaging-relevant component can be moved and/or is mounted such that it can move. It is conceivable that the imaging-relevant component has a plurality of degrees of freedom of movement, such as, for example, two, three, four or more degrees of freedom. It is equally conceivable that the mechanical guide has a pivot joint or a ball joint that enables substantially three-dimensional movement of the imaging-relevant component in a limited range of motion.

The mechanical guide is embodied to enable manual positioning of the imaging-relevant component along the at least one degree of freedom of movement. The mechanical guide preferably has a handpiece for this purpose. The handpiece can, for example, be embodied as a handle or a rod of any shape that is used by the user of the imaging apparatus in order to move the imaging-relevant component manually into the application-appropriate position along a degree of freedom of movement. The mechanical guide can moreover have a force-reducing mechanism, such as, for example, a lever or a pulley block that reduces a force to be applied by the user during the positioning of the imaging-relevant component.

The computing unit of the imaging apparatus is preferably embodied to process any analog and digital signals and/or information and can, for example, comprise a processor, microprocessor, CPU, GPU or the like. The computing unit can further have a controller or microcontroller configured to acquire, output and/or convert analog signals and/or digital signals. The computing unit can furthermore have an electronic and/or magnetic memory, such as, for example, a RAM, ROM, PROM, EPROM, EEPROM, Flash, but also HDD, SSD or further memory types. It is equally conceivable that the computing unit has a suitable interface by which the computing unit can access an external memory, such as, for example, a database, cloud, server or any other storage medium. Herein, the computing unit is preferably connected to the external memory via a network interface, bus interface and/or via an analog signal connection. In a preferred embodiment of the imaging apparatus, the computing unit is electrically and mechanically connected to the control unit of the imaging apparatus.

The at least one sensor is embodied to acquire a position of the target region of the patient relative to the imaging-relevant component. As described above, the sensor for acquiring the relative position can be embodied as a camera, which, for example, records two-dimensional and/or three-dimensional image data of the target region of the patient.

The sensor can furthermore be embodied as a distance sensor, which acquires the distance between the imaging-relevant component and the surface of the target region of the patient. In one preferred embodiment, the imaging apparatus has a plurality of cameras and/or distance sensors in order to ascertain the position of the target region of the patient relative to the imaging-relevant component. In addition to detecting the distance between the target region of the patient and the imaging-relevant component, the plurality of sensors can in particular also be suitable for detecting an angle and/or alignment of the imaging-relevant component with respect to the target region of the patient.

The computing unit of the imaging apparatus is embodied to determine the application-appropriate position of the imaging-relevant component and to derive a positioning instruction at least in dependence on the position of the patient relative to the imaging-relevant component, wherein the output interface is configured to output the positioning instruction. As described above, the determination of the application-appropriate position can be performed via the computing unit in dependence on intelligent algorithms, the body model and external data, patient information or the like. To determine the positioning instruction, the computing unit is preferably embodied to determine a trajectory of the imaging-relevant component along the degree of freedom of movement or the plurality of degrees of freedom of movement. The degrees of freedom of movement of the imaging-relevant component are usually predetermined for a given imaging apparatus and can, for example, be read in from a database or a memory via the computing unit.

Herein, the positioning instruction is derived at least in dependence on the position of the patient relative to the imaging-relevant component. For this purpose, in one possible embodiment, the computing unit has, for example, an image-processing algorithm embodied to recognize the imaging-relevant component and the patient and/or the target region of the patient in the image data from a camera and to determine a spatial distance to be covered by the imaging-relevant component. The image-processing algorithm can further be configured to identify immobile or foreign objects between the imaging-relevant component and the patient so that the computing unit can take account of the immobile or foreign object when determining the positioning instruction and, for example, bypass the object. Herein, an immobile or foreign object can constitute a further component of the imaging apparatus, a person, a part of the examination room or the like.

An output interface for outputting the positioning instruction can be embodied to output analog and/or digital signals. Such signals can in particular constitute image data, video data and/or control signals. The output interface can further be embodied to transmit the positioning instruction by wireless device(s), for example via a radio connection, Bluetooth connection and/or WLAN connection, to any display unit.

The user of the imaging apparatus can advantageously be assisted in the positioning of the imaging-relevant component on the basis of the output of the positioning instruction on a display unit. This can accelerate the positioning sequence and advantageously avoid incorrect positioning of the imaging-relevant component.

In a further embodiment of the imaging apparatus according to the invention, the at least one sensor is embodied to acquire a position of the imaging-relevant component relative to the imaging apparatus, wherein the computing unit is embodied to determine the application-appropriate position of the imaging-relevant component at least in dependence on the position of the imaging-relevant component relative to the imaging apparatus. This embodiment is in particular relevant in the case of imaging apparatuses with which the patient is moved continuously, or continuously in sections, in an approximately constant position on the patient table through the imaging apparatus and herein is at least partially masked thereby. Here, for example, the position of the patient table relative to the imaging apparatus can be acquired (instead of or additionally to the position of the target region of the patient relative to the imaging-relevant component) in order to determine the positioning instruction.

As described above, herein, the at least one sensor of the imaging apparatus can be embodied as a camera or a distance sensor. However, it is in particular conceivable that at least one sensor is embodied as an incremental encoder, which, for example, measures a deflection of the patient table and/or a position of the patient table (or another imaging-relevant component) relative to the imaging apparatus. In one preferred embodiment, the computing unit is configured to determine the positioning instruction in dependence on a measured value from the incremental encoder and the image data from the camera. For this purpose, the computing unit can have an image-processing algorithm that determines the position of the patient on the patient table based on image data from the camera as part of a reference measurement. The image-processing algorithm is preferably configured to ascertain a target region of the patient in relation to the patient table and/or to register it in the image data with the patient table. The acquisition of image data via the camera can, for example, be performed once as a reference measurement even before the patient table is positioned in the application-appropriate position. The computing unit can further be configured to read in measurement data from the incremental encoder in order to determine a position of the patient table in relation to the imaging apparatus. A horizontal path distance and/or a vertical path distance required to achieve the application-appropriate position can, for example, be determined in dependence on the position of the target region of the patient on the patient table and the position of the patient table in relation to the imaging. The positioning instruction can then be derived based on the horizontal path distance and/or the vertical path distance. Of course, the at least one sensor can be configured to acquire relative positions between any further imaging-relevant components and the imaging apparatuses. Herein, the imaging-relevant components can have any kind of mechanical guide, such as, for example, a rail system, a telescope system, a pivot joint, a ball joint or the like that enable movement of the imaging-relevant component relative to the imaging apparatus.

Recording a reference measurement to determine the position of the target region of the patient relative to the imaging-relevant component advantageously enables the positioning instruction to be determined based on measured values from an incremental encoder that acquires the position of the imaging-relevant component relative to the imaging apparatus. This advantageously enables masking of the target region of the patient during movement into the imaging apparatus to be compensated. In addition, the use of an incremental encoder can enable a particularly time-efficient and accurate ascertainment of the position of the imaging-relevant component relative to the imaging apparatus to be achieved.

In a further embodiment, the imaging apparatus according to the invention has a braking apparatus configured to limit the at least one degree of freedom of movement of the imaging-relevant component at a position predetermined by the positioning instruction and/or to lock the imaging-relevant component in the application-appropriate position in dependence on the positioning instruction. A braking apparatus can have a brake pad, which, upon transfer to a locking position, is brought into contact with the imaging-relevant component and forms a force-fitting connection with the imaging-relevant component. The braking apparatus can also have a plurality of brake pads embodied to contact the imaging-relevant component on one or more sides and herein to reduce the kinetic energy of the imaging-relevant component. The force-fitting connection between the brake pad and the imaging-relevant connection can preferably be modulated. This can mean that the speed of transfer of the braking apparatus into the locking position and/or a braking force exerted by a brake pad onto a surface of the imaging-relevant component can be changed by way of the positioning instruction. Herein, the positioning instruction can in particular have a control signal which is generated by the computing unit of the imaging apparatus and transmitted to the braking apparatus via the output interface via a suitable signal connection.

It is further conceivable that the braking apparatus forms a form-fitting connection with the imaging-relevant component in the locking position. In one embodiment, to create a form-fitting connection, the braking apparatus can have a stop element, such as, for example, a pin, a bolt, a spring, an elastic body or the like, which is transferred to a stop position in dependence on the control signal. Herein, the stop element can interact and/or engage with a complementary stop element of the imaging-relevant component, such as, for example, a bolt, pin, grid, hole matrix, hollow cylinder, shell or the like, in order to provide a form-fitting connection.

The braking apparatus is in particular embodied to limit at least one degree of freedom of movement of the imaging-relevant component at a position predetermined by the positioning instruction. This can mean that the braking apparatus is configured to change the stop position of a stop element and/or the locking position of a brake pad along a degree of freedom of movement of the imaging-relevant component in dependence on the control signal of the positioning instruction.

The braking apparatus is furthermore embodied to lock the imaging-relevant component in the application-appropriate position in dependence on the positioning instruction. This can mean that, after the braking apparatus has been transferred into the locking position by the application of manual force by the user of the imaging apparatus, the imaging-relevant component is substantially immobile.

The provision of the braking apparatus also advantageously enables accurate positioning of the imaging-relevant component in dependence on the positioning instruction when the imaging-relevant components are manually moved by the user.

In one possible embodiment, the imaging-relevant component of the imaging apparatus according to the invention has a motor element embodied to correct a minor positioning error of the imaging-relevant component in dependence on the positioning instruction and to move the imaging-relevant component into the application-appropriate position along the at least one degree of freedom of movement. A motor element can have a drive embodied to move the imaging-relevant component along a degree of freedom of movement. A drive can for example be a hydraulic, pneumatic, motorized and/or electric drive that converts internal energy of a drive medium and/or electric energy into kinetic energy of the imaging-relevant component. The motor element is preferably undersized with respect to a maximum possible deflection of the imaging-relevant component along a degree of freedom of movement. This can mean that a range, force and/or speed of the motor element is only suitable for transporting the imaging-relevant component along a limited path distance. Herein, a limited path distance can, for example, be a few millimeters to several centimeters. However, it is equally conceivable that a speed of movement of the imaging-relevant component is limited via the motor element. In particular, fully automated movement of the imaging-relevant components from a starting position into the application-appropriate position via the motor element may be uneconomical for the usual workflow of the imaging apparatus.

The motor element is preferably embodied to correct minor positioning errors that remain during manual positioning of the imaging-relevant component by the user of the imaging apparatus. The computing unit can be embodied to acquire minor positioning errors of the imaging-relevant component via the at least one sensor and to transmit a corresponding positioning instruction to the motor element by way of the control signal. The motor element preferably has a typical interface, such as, for example, an analog 0-10 V or 0-24 mA interface, a digital interface or a bus interface in order to acquire the control signal and correct the position of the imaging-relevant component accordingly.

The motor element advantageously enables a minor positioning error of the imaging-relevant component to be corrected during manual positioning by the user. The use of motor elements that are only suitable for correcting minor positioning errors advantageously further enables manufacturing costs and operating costs to be reduced compared to a fully automated imaging apparatus with more costly motor elements.

In a further embodiment, the imaging apparatus according to the invention has a display unit, wherein the display unit has a signal connection to the output interface and is configured to output a positioning instruction to a user of the imaging apparatus. A display unit can be any device suitable for outputting optical, acoustic and/or haptic signals. A haptic signal can, for example, constitute vibration or comparable force feedback. The display unit is preferably embodied as a monitor embodied to display the positioning instruction on a video screen for the user of the imaging apparatus. However, the display unit can also be a projector that projects the positioning instruction onto a wall or a projection screen. It is further conceivable that the display unit is a tablet, smartphone or comparable portable device.

The display unit is preferably embodied to depict the positioning instruction and/or image data acquired via the camera. Herein, the positioning instruction can comprise the map of the examination room with the current positions of the imaging-relevant component, the patient and the imaging apparatus, but also the application-appropriate position of the imaging-relevant component. It is furthermore conceivable that, as described above, the application-appropriate position of the imaging-relevant component is registered as a schematic drawing in the map of the examination room or superimposed thereupon. The map on the display unit (positioning instruction) enables the user of the imaging apparatus to move the imaging-relevant component into the application-appropriate position.

In a further embodiment, the display unit can be embodied as an indication element or a plurality of indication elements. An indication element can constitute any object that encodes information in the form of an optical, acoustic and/or haptic signal. An indication element can, for example, have a lighting device(s) embodied to light up and/or to change a wavelength of the emitted light in dependence on the positioning instruction. In a simple example, the indication element is embodied as an arrow which is illuminated by way of a LED in dependence on a control signal of the positioning instruction. The arrow can, for example, light up green in dependence on the positioning instruction if the patient table is to be moved in a direction corresponding to the arrow. When the application-appropriate position of the imaging-relevant component is achieved, the illumination of the indication element can be terminated accordingly. It is conceivable that the display unit comprises a plurality of indication elements which can be illuminated in a different order, a different pattern or different colors in dependence on the positioning instruction.

The display unit can further be embodied to encode information from the positioning instruction via a variable property of the optical, acoustic and/or haptic signal. Herein, the encoding of the positioning instruction can in particular be performed by changing a signal intensity and/or a signal frequency. This can, for example, comprise a frequency of an acoustic tone, a color value of an illumination and a duration of a pause between acoustic tones and/or vibration pulses and/or light pulses or the like. Herein, the signal intensity and/or the signal frequency can, for example, vary in dependence on the distance between the imaging-relevant component and the application-appropriate position and/or the current speed of the imaging-relevant components.

The provision of a display unit for outputting the positioning instruction to the user of the imaging apparatus enables the above-described advantages of sensor-based acquisition of the relative positions of the imaging-relevant component, the patient and/or the imaging apparatus to be combined with manual positioning of the imaging-relevant component by the user of the imaging apparatus. This advantageously enables accurate and time-efficient positioning of the imaging-relevant component in the application-appropriate position to be achieved. Furthermore, the imaging-relevant component can advantageously be positioned by an untrained user since the application-appropriate position of the imaging-relevant component is automatically ascertained and output to the user. The encoding of the positioning instruction by way of a signal intensity and/or a signal frequency further enables direct feedback to a sensory capability of the user to be achieved and thus the user is advantageously informed immediately about a current positioning status.

In one possible embodiment, the display unit of the imaging apparatus according to the invention is shaped like a body region of the user of the imaging apparatus and can be fastened to the body region of the user. This can mean that the display unit partially or completely encloses a body region of the user, such as, for example, a leg, arm, wrist, head or the like. Herein, the display unit can have a fastening element that reversibly connects the display unit to the body region of the user. Such a fastening element can, for example, comprise a tension belt, strap, waist belt, Velcro fastener, zipper, button, clip or the like which connect the display unit to the body region in a force-fitting and/or form-fitting manner with the body region. In one embodiment, the display unit is embodied as a smartwatch which outputs the positioning instruction to the user in the form of acoustic signals and/or vibrations. The smartwatch can have a wristband embodied to fasten the smartwatch to the user's wrist. In a further embodiment, the display unit can be embodied as VR glasses that can be positioned in the user's field of view. In this context, VR glasses are also considered to be AR (augmented reality) glasses and MR (mixed reality)

glasses. Accordingly, VR glasses can be configured to generate image data entirely digitally, superimpose image data onto a physical image of a scene or a field of view and/or to enable interaction with physical objects in a virtual world or in the image data. The VR glasses preferably have a projector that displays the positioning instruction on an inner surface of the VR glasses facing an eye of the user. The VR glasses preferably have a transparent viewing lens so that the user can view the examination room through the viewing lens of the VR glasses. In this case, the projector is in particular configured to project a schematic drawing of the imaging-relevant component in the user's field of view such that the schematic drawing is mapped in the application-appropriate position in relation to the imaging apparatus and/or the target region of the patient. Instead of the transparent viewing lens, the VR glasses can equally have a screen. The screen is preferably positioned in the user's field of view and embodied to display the map of the examination room and the schematic drawing of the imaging-relevant component in the application-appropriate position together to the user.

The display unit can likewise be embodied to output the positioning instruction as an acoustic signal and/or force feedback to the user of the imaging apparatus. With reference to the above examples, the smartwatch can, for example, be configured to transmit a vibration to the user's wrist. In a further example, the VR glasses have a speaker which, when the VR glasses are worn in an application-appropriate manner, is positioned close to the user's ear. The VR glasses' speaker can be embodied to output the positioning instruction by way of acoustic signals, such as, for example, a voice instruction or an acoustic tone, to the user. In addition, any further embodiments of display units which can be fastened to the user of the imaging apparatus and are configured to output optical, acoustic and/or haptic signals to the user are conceivable.

The provision of a display unit that is shaped like the body region of the user enables the user to position the imaging-relevant component in the application-appropriate position independently of a statically installed display unit. This advantageously avoids the need for the user to be constantly oriented in the direction of the statically installed display unit. Moreover, improved focusing of the user on the positioning of the imaging-relevant component can reduce the risk of incorrect positioning.

The computer program product according to at least one embodiment of the invention can be loaded into a memory of the computing unit of the imaging apparatus and has program code in order to execute a method according to at least one embodiment of the invention when the computer program product is executed in the computing unit of the imaging apparatus.

The computer program product according to at least one embodiment of the invention enables the method according to at least one embodiment of the invention to be executed in a rapid, identically repeatable and robust manner. The computer program product is configured such that it can execute the method steps according to the invention via the computing unit. Herein, the computing unit must in each case fulfil the requisite conditions such as, for example, an appropriate random-access memory, an appropriate graphics card or an appropriate logic unit so that the respective method steps can be executed efficiently. The computer program product is, for example, stored on a computer-readable medium or held on a network, server or cloud from where it can be loaded into the processor of a local computing unit, which is embodied as a standalone system component or as part of the imaging apparatus. Furthermore, control information of the computer program product can be stored on an electronically readable data carrier. The control information of the electronically readable data carrier can be embodied such that it carries out a method according to the invention when the data carrier is used in the computing unit of the imaging apparatus. Examples of electronically readable data carriers are a DVD, a magnetic tape, a USB stick or any other memory on which electronically readable control information, in particular software, is stored. When this control information is read from the data carrier and stored in a control unit and/or computing unit of the imaging apparatus according to the invention, all the embodiments according to the invention of the above-described embodiments of the method according to the invention can be carried out.

FIG. 1 shows a possible embodiment of an imaging apparatus according to the invention. In the present case, the imaging apparatus is embodied as an X-ray apparatus 1 with a C-arm 6 on which an X-ray source 7 and an X-ray detector 8 are arranged opposite one another. The X-ray source 7 and the X-ray detector 8 together form an emitter/detector arrangement, constituting an imaging-relevant component of the X-ray apparatus 1. The C-arm 6 of the X-ray apparatus 1 is aligned such that a target region 9 of a patient 15 positioned on a patient table 17 can be recorded. The C-arm 6 can be used to move the X-ray source 7 and the X-ray detector 8 into different recording positions with respect to the patient 15 mounted on the patient table 17. For this purpose, the X-ray apparatus 1 can be moved along the spatial directions X and Z via a mobile carrier unit 2. The C-arm 6 also has a pivot joint 31 which enables rotation of the C-arm 6 along the direction of rotation Wz. The C-arm 6 is further mounted on the pivot joint 31 via a rail system 32 so that the C-arm 6 can be displaced along the direction of rotation Wz.

The alignment of the emitter/detector arrangement with respect to the target region 9 of the patient 15 is performed primarily via the degrees of freedom of movement of the C-arm 6 along the directions of rotation Wz and Wy and the degrees of freedom of movement of the mobile carrier unit 2 along the spatial directions X and Z. For this purpose, the user 29 of the X-ray apparatus 1 can move the C-arm 6 and the mobile carrier unit 2 manually along the degrees of freedom of movement into the application-appropriate position. In addition, the patient table 17 can of course be positioned along the spatial directions X and Z and a height Y. In the embodiment shown in FIG. 1, the patient table 17 has a motor element 61. The motor element 61 is embodied to move the patient table 17 in dependence on a control signal of the positioning instruction along the spatial direction Y by a limited path distance. In the example shown, the control signal is transmitted to the motor element 61 via the output interface 43 via the signal connection 64c. This enables minor positioning errors of the patient table 17 to be corrected and the target region 9 of the patient 15 to be positioned in the application-appropriate position between the X-ray source 7 and the X-ray detector 8.

In the present embodiment, both the patient table 17 and the emitter/detector arrangement with the X-ray source 7 and the X-ray detector 8 are imaging-relevant components. To acquire medical image data of the target region 9 of the patient 15, the imaging-relevant components must be positioned in a predetermined position relative to one another and to the patient 15. To determine current positions of the imaging-relevant components, the X-ray apparatus 1 has two sensors 63a and 63b. In the embodiment shown, the sensor 63*a* is embodied as a 3D camera 63*a* which acquires a three-dimensional map of the examination room with the X-ray apparatus 1, the patient 15 and the patient table 17. The three-dimensional map of the examination room is transmitted to the computing unit 40 as an analog or digital signal via the signal connection 64*a* and the control unit 4 and processed. The processing of the three-dimensional map of the examination room can, for example, comprise the detection of reference points on the emitter/detector arrangement, the patient table 17 and/or the patient 15, which enable the distance and/or the alignment between the imaging-relevant components and the patient 15 to be determined. In the embodiment shown, the X-ray apparatus 1 also has a distance sensor 63*b*, which acquires the distance 65 between the X-ray source 7 and the target region 9 of the patient 15. The distance 65 can, for example, be used as a reference value which increases the accuracy of the determination of the relative positions of the imaging-relevant components and the patient 15 based on the three-dimensional map of the examination room.

The computing unit 40 of the X-ray apparatus 1 is embodied to determine the application-appropriate positions of the emitter/detector arrangement and the patient table 17 based on the data from the sensors 63*a*, 63*b* and the target region 9 of the patient 15 and to ascertain a positioning instruction which is output to the display unit 41*a*. In the example shown, the display unit 41*a* is embodied as VR glasses, which are positioned on the head of the user 29 of the X-ray apparatus 1 and have a transparent viewing lens. In the present example, the user 29 is an attending medical professional. The positioning instruction comprises, for example, schematic drawings of the patient table 17, the emitter/detector arrangement and the C-arm 6 in the respective application-appropriate position. These schematic drawings are projected onto the viewing lens of the VR glasses and enable the user 29 to move the patient table 17 and the C-arm 6 with the X-ray source 7 and the X-ray detector 8 into the application-appropriate positions. Herein, the schematic drawings of the imaging-relevant components are projected onto the viewing lens of the VR glasses such that the application-appropriate positions of the imaging-relevant components are positioned in a correct spatial arrangement with respect to the section of the examination room that the user 29 observes through the viewing lens of the VR glasses. Instead of the projector, the VR glasses can of course also have electronic components, a transparent electronic circuit, an optical fiber display or the like with which the schematic drawing can be output on the viewing lens of the VR glasses.

The X-ray apparatus 1 further has a control unit 4 embodied to control the X-ray apparatus 1. The tasks of the control unit 4 can in particular comprise setting various imaging parameters, coordinating various steps of the image recording and image processing, transmitting data from the sensors 63*a* and 63*b* to the computing unit 40 and outputting the positioning instruction to the display unit 41*a* and the control signal to the motor element 61. In the present embodiment, the computing unit 40 is integrated in the X-ray apparatus 1 and connected to the control unit 4.

In the example shown, the signal connection between the display unit 41*a* and the computing unit 40 or the control unit 4 is embodied by wireless device(s) in order to avoid the restriction of the radius of action and/or the freedom of movement of the user 29 by a cable. For this purpose, the output interface 43 has, for example, a WLAN interface, a Bluetooth interface and/or a radio interface. Furthermore, in the present embodiment, the output interface 43 is embodied to transmit the positioning instruction and the schematic drawings of the imaging-relevant components by wireless device(s) in the application-appropriate position to the corresponding interface of the VR glasses 41*a*.

Figure 2:
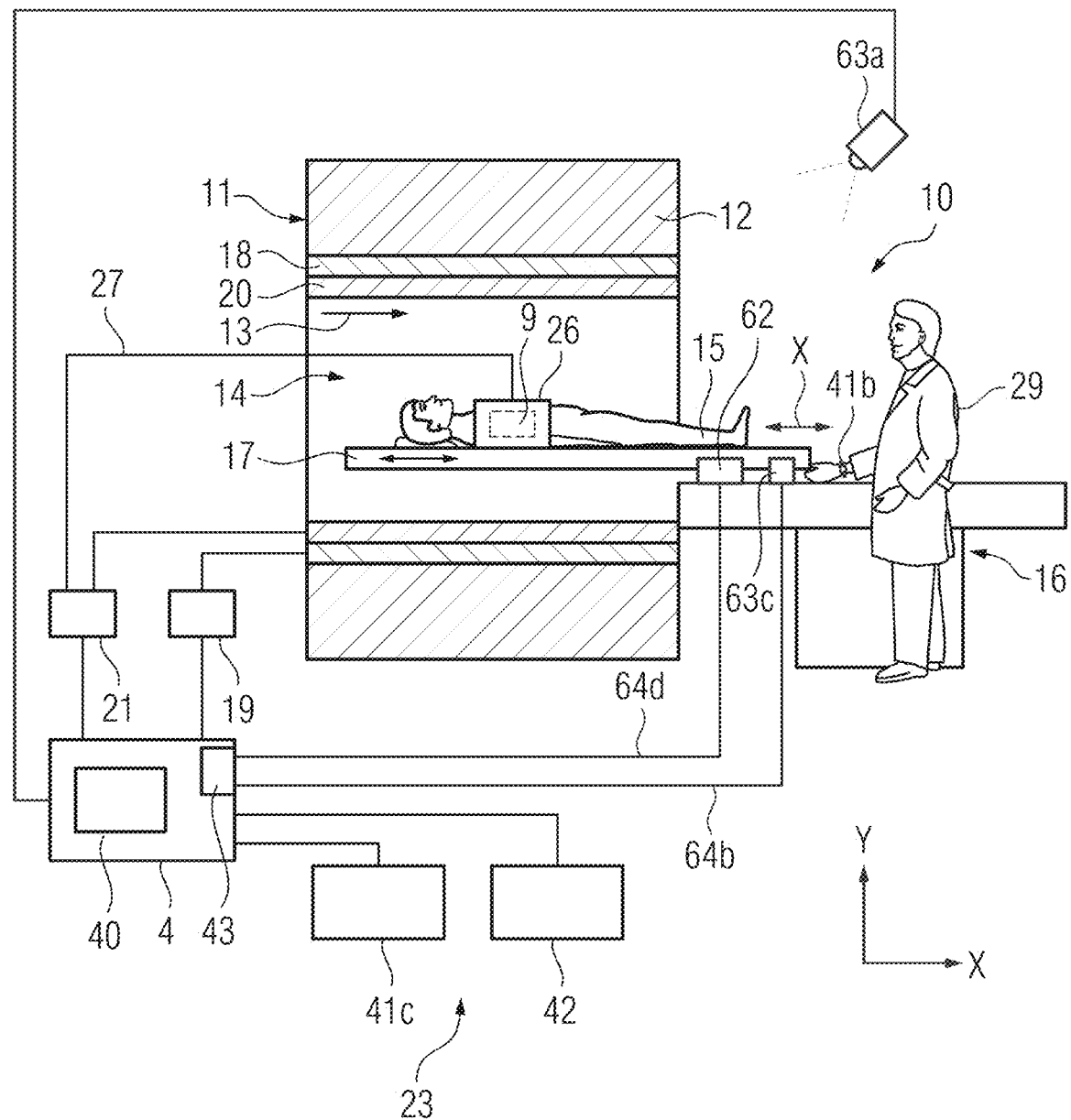
FIG. 2 shows an embodiment of an imaging apparatus according to the invention.

FIG. 2 shows a further embodiment of the imaging apparatus according to the invention. In this example, the imaging apparatus is a magnetic resonance apparatus 10 with a magnet unit 11 having, for example, a permanent magnet, an electromagnet or a superconducting main magnet 12 for generating a strong and in particular homogeneous main magnetic field 13. Moreover, the magnetic resonance apparatus 10 comprises a patient-receiving region 14 for receiving a patient 15. In the present example embodiment, the patient-receiving region 14 is cylindrical in shape and surrounded by the magnet unit 11 in a circumferential direction. However, in principle, embodiments of the patient-receiving region 14 that differ from this example are equally conceivable.

The patient 15 can be positioned in the patient-receiving region 14 via a patient-mounting apparatus 16 of the magnetic resonance apparatus 10. For this purpose, the patient-mounting apparatus 16 has a patient table 17 that is movable within the patient-receiving region 14. The magnet unit 11 furthermore has a gradient coil 18 for generating magnetic field gradients which are used for spatial encoding during imaging. The gradient coil 18 is actuated via a gradient control unit 19 of the magnetic resonance apparatus 10. The magnet unit 11 can furthermore comprise a radio-frequency antenna, which, in the present example embodiment, is embodied as a body coil 20 permanently integrated in the magnetic resonance apparatus 10. The body coil 20 is configured to excite atomic nuclei located in the main magnetic field 13 generated by the main magnet 12. The body coil 20 is actuated by a radio-frequency unit 21 of the magnetic resonance apparatus 10 and radiates radio-frequency signals into an examination room substantially formed by a patient-receiving region 14 of the magnetic resonance apparatus 10. The body coil 20 is furthermore embodied to receive magnetic resonance signals from the patient 15.

To control the main magnet 12, the gradient control unit 19 and to control the radio-frequency unit 21, the magnetic resonance apparatus 10 has a control unit 4. The control unit 4 is embodied to control the execution of a sequence, such as, for example, an imaging gradient echo sequence or a turbo spin-echo sequence. In the example shown, the control unit 4 moreover comprises the computing unit 40, which is embodied to evaluate digitized magnetic resonance signals acquired during the magnetic resonance examination. The computing unit 40 and the control unit 4 are further embodied to acquire and process digital and/or process analog signals from the sensors 63*a* and 63*c*.

In the present example, the computing unit 40 is in particular embodied to determine the positioning instruction for the patient table 17 at least in dependence on information on the target region 9 of the patient 15 and the data and/or signals from the sensors 63*a* and 63*c* and to output this to the display unit 41*b* via the output interface 43. In the example shown, the display unit 41*b* is embodied as a smartwatch which is fastened to the wrist of the user 29 and outputs the positioning instruction by way of vibration pulses. As described above, in this example, the output interface 43 is also embodied to transmit the positioning instruction by wireless device(s) to the display unit 41*b*.

In the example depicted, the sensor 63*c* is an incremental encoder which acquires the current position of the patient table 17 in dependence on the deflection relative to the patient-mounting apparatus 16. The sensor 63c can transmit the information on the current position of the patient table 17 to the computing unit 40 and/or the control unit 4 by wireless device(s) or in a wired manner (not shown). The combination of data from the 3D camera 63a and the incremental encoder 63c enables the accuracy of the determination of the current position of the patient table 17 and hence also the accuracy of the positioning instruction to be increased compared to a purely image-processing-based determination of the positioning instruction based on image data from the 3D camera 63a.

In the embodiment shown, the magnetic resonance apparatus 10 has the braking apparatus 62, which is electrically connected to the output interface 43 via the signal connection 64d. The braking apparatus 62 can, for example, have a brake pad (not shown) which, when the braking apparatus 62 is actuated, is transferred to a locking position or released from the locking position in dependence on the positioning instruction. The computing unit 40 is preferably embodied to determine the point in time of the actuation of the braking apparatus 62 in dependence on the current kinetic energy of the patient table 17. The current kinetic energy of the patient table 17 with the patient 15 can, for example, be ascertained from the speed and the mass of the patient table 17 and the patient 15. Herein, the patient-mounting apparatus 16 can have a further sensor for acquiring the weight of the patient table 17 and/or the patient 15. However, it is equally conceivable that the computing unit 40 reads the weight of the patient 15 and the patient table 17 from the patient information and/or an external database. The computing unit 40 is furthermore embodied to determine the current speed with which the user 29 displaces the patient table 17 along the degree of freedom of movement X based on the data from the incremental encoder 63c and/or the 3D camera 63a.

The computing unit 40 can further be embodied to determine a point in time and a force with which the braking apparatus 62 is to be transferred into the locking position and to actuate the braking apparatus 62 accordingly via a control signal. This enables the patient table 17 to be stopped and locked in the application-appropriate position by the braking apparatus 62 from any movement. In addition, further possibilities for determining the point in time and/or the force of the locking of the braking apparatus 62 are conceivable. In one example, the patient table 17 can have a sensor for acquiring the force exerted by the user 29 on the patient table 17 in order to determine the kinetic energy of the patient table 17. It is equally conceivable that the braking apparatus 62 has a stop element which can be positioned along the degree of freedom of movement X of the patient table 17 and terminates a movement of the patient table 17 in the application-appropriate position. In this case, it is possible to dispense with the determination of the kinetic energy of the patient table 17.

In addition, the magnetic resonance apparatus 10 comprises a user interface 23 with a signal connection to the control unit 4. The display unit 41c of the user interface 23 is preferably embodied as a monitor configured to display medical image data from the target region 9 of the patient 15 to the user 29. It is equally conceivable that the display unit 41c has a graphical user interface for setting imaging parameters of the magnetic resonance apparatus 10. The user interface 23 can in particular comprise an operator control unit 42 by which parameter sets of the magnetic resonance apparatus 10 can be adapted by the user 29. The user interface 23 can further provide a possibility for starting, ending and/or parameterizing the method according to the invention. Finally, the display unit 41c can also be embodied to output positioning instructions for the imaging-relevant component to the user 29.

The magnetic resonance apparatus 10 furthermore comprises a local coil 26, which is positioned on the target region 9 of the patient 15 and transmits magnetic resonance signals from the target region 9 of the patient 15 to the magnetic resonance apparatus 10. The local coil 26 has an electrical connection line 27, which provides a signal connection with corresponding receiver channels of the radio-frequency unit 21 and the control unit 4. The receiver channels filter and digitize the signal received from the local coil 26 and transfer the data to the computing unit 40, which derives an image or spectrum from the data and makes it available to the user 29 of the imaging apparatus via the display unit 41c.

FIG. 3 shows a further embodiment of the imaging apparatus according to the invention. In this embodiment, the imaging apparatus is embodied as a Bucky wall stand 70 having an X-ray source 7 and an X-ray detector 8 in a spatially separated arrangement. The X-ray source 7 is supported by a ceiling beam 71, which is mounted via a rail system 72a, 72b and a telescope system 74 such that it can move in three spatial directions. In the example shown, the X-ray source 7 has at least five degrees of freedom of movement by which the X-ray source 7 can be aligned with the target region 9 of the patient 15. The at least five degrees of freedom of movement comprise three translational degrees of freedom of movement along the spatial directions X, Y and Z and two rotational degrees of freedom of movement about the directions of rotation Wz and Wy. It is in particular conceivable that the X-ray source 7 has at least one sixth degree of freedom of movement, which is defined by a positioning and/or alignment of a collimator of the X-ray source 7 relative to the X-ray tube.

The X-ray detector 8 of the Bucky wall stand 70 is connected to a wall bracket 73 via a rail system 72c. The rail system 72c enables vertical displacement of the X-ray detector 8 along the wall bracket 73 in order to enable the position of the X-ray detector 8 to be adapted to the target region 9 of the standing patient 15.

In the example shown, the sensor 63 of the Bucky wall stand 70 is embodied as a 3D camera 63a. The 3D camera 63a is mounted on the wall and embodied to record three-dimensional image data of the examination room with the X-ray source 7, the ceiling beam 71, the wall bracket 73, the detector 8 and the patient 15. In FIG. 3, the position of the 3D camera 63a is chosen arbitrarily. The 3D camera 63a can be installed in any position that enables at least one common acquisition of the Bucky wall stand 70 and the patient 15. However, it is equally conceivable that the Bucky wall stand 70 has a plurality of cameras, which are aligned with individual objects in the examination room, such as, for example, the X-ray source 7, the X-ray detector 8 and/or the patient 15. Herein, the image data from the camera can be transferred by the computing unit 40 (not shown) into a common two-dimensional or three-dimensional map of the examination room. The plurality of cameras can in particular also be embodied as 2D cameras and/or infrared cameras and/or positioned directly on the X-ray source 7 and/or the wall bracket 73.

In the embodiment shown, the user 29 of the Bucky wall stand 70 has to transfer the X-ray source 7 and the X-ray detector 8 into an application-appropriate position separately from one another in order to record medical image data from the target region 9 of the patient 15. Herein, the application-appropriate positions of the X-ray source 7 and the X-ray detector 8 are preferably determined in dependence on patient information and/or a body model, which is adapted to the patient 14 with image data from the 3D camera 63a. However, as described above, the use of intelligent algorithms that determine the application-appropriate position of the X-ray source 7 and the X-ray detector 8, in dependence on patient information, the body model and/or the image data from the 3D camera 63a is also conceivable.

In the embodiment depicted, the wall bracket 73 of the X-ray detector 8 has two indication elements 81a and 81b, which output a positioning instruction to the user 29. For this purpose, the indication elements 81a and 81b have lighting device(s) which light up in dependence on the positioning instruction and encode information from the positioning instruction. The indication elements 81a and 81b are embodied by way of example as arrows indicating a direction of the positioning of the X-ray detector 8. In the example depicted, the indication element 81a lights up because the user 29 is to move the X-ray detector 8 upward in a vertical direction along the wall bracket 73 in order to establish the application-appropriate position. In contrast, the indication element 81b can light up when the user 29 is to move the X-ray detector 8 downward in the vertical direction. Once the X-ray detector 8 is in the application-appropriate position neither of the two indication elements 81a and 81b is illuminated.

In the embodiment shown, the user 29 manually transfers the X-ray detector 8 into the application-appropriate position in dependence on the positioning instruction from the indication elements 81a and 81b. It is conceivable that the X-ray source 7 also has indication elements for outputting the positioning instruction. However, due to the high number of degrees of freedom of movement, the positioning instruction for the X-ray source 7 is preferably output to the user 29 via VR glasses. It is equally conceivable that the ceiling beam 71 of the X-ray source 7 has at least one motor element 61 and/or a braking apparatus 62 in order to correct minor positioning errors along one or more degrees of freedom of movement and/or to lock the X-ray source 7 in an application-appropriate position along one or more degrees of freedom of movement.

FIG. 4 shows a possible flow diagram of a method according to an embodiment of the invention for positioning an imaging-relevant component of an imaging apparatus in an application-appropriate position for recording medical image data from a target region 9 of a patient 15, wherein the imaging-relevant component of the imaging apparatus is moved relative to a static arrangement of the imaging apparatus and/or the patient 15 in order to achieve imaging coordinated with the target region 9 of the patient 15.

In a step S1, information on the target region 9 of the patient 15 is acquired. The information on the target region 9 of the patient 15 can, for example, be entered by an attending medical professional 29 on an operator control unit 42 of the imaging apparatus. Herein, the input can be performed via any input device, such as, for example, a keyboard, mouse, controller, but also via voice control. It is equally conceivable that the information on the target region 9 of the patient 15 is queried or read in via a network from a RIS or HIS. The attending medical professional 29 can, for example, retrieve this information manually from a database. It is furthermore conceivable that the computing unit 40 of the imaging apparatus is embodied to retrieve the information on the target region 9 automatically from a database based on a corresponding search word, such as, for example, the name of the patient 15, a diagnosis, a body region or the like. During the acquisition of the information on the target region 9 of the patient 15, it is in particular also possible for further data, such as, for example, patient information, image data and/or additional information on the imaging-relevant component and/or the imaging apparatus to be read in.

In a step S2, a position of the patient 15 relative to the imaging-relevant component is acquired. The acquisition of the position of the patient 15 relative to the imaging-relevant component can, for example, be performed via optical sensors, such as a 3D camera 63a, 2D camera or infrared camera. The computing unit 40 preferably has an image-processing algorithm embodied to determine the position of the patient 15 relative to the imaging-relevant component. This can, for example, be based on natural reference points on the imaging-relevant component and the patient 15. Examples of such reference points constitute the head, nose and/or eyes of the patient 15 and the geometric dimensions of the patient table 17 and/or a C-arm 6 of an X-ray apparatus 1. However, it is equally conceivable that the relative position between the imaging-relevant component and the patient 15 is determined on the basis of distance sensors 63b and/or incremental encoders 63c. A distance sensor 63b on the imaging-relevant component can be used to measure the position relative to the patient 15 directly via the distance 65. An incremental encoder 63c is preferably used to determine the relative position between the imaging-relevant component and the imaging apparatus. During the determination of the positioning instruction in dependence on data from the incremental encoder 63c, preferably at least one reference measurement is performed via a further sensor in order to determine the relative position between the imaging-relevant component, such as, for example, the patient table 17 and the target region 9 of the patient 15.

In a further step S3, the application-appropriate position of the imaging-relevant component is determined in dependence on the information on the target region 9 of the patient 15. The determination of the application-appropriate position of the imaging-relevant component can, for example, be performed based on information on the target region 9 of the patient acquired in step S1. It is conceivable that, for a large number of diagnostic issues, application-appropriate positions which have become established in clinical practice are already held in a database, a network or the RIS or HIS. The determination of the application-appropriate position of the imaging-relevant component can furthermore also be performed in dependence on a body model. The body model can, for example, comprise information on typical positions and/or dimensions of relevant organs in a human body. In one preferred embodiment, the body model can be adapted or scaled accordingly with respect to individual properties of the patient 15 by way of patient information, such as, for example, the height, gender and/or weight of the patient 15.

The application-appropriate position of the imaging-relevant component is preferably determined via the computing unit 40. Herein, the computing unit 40 can access additional information on the imaging-relevant component and/or the imaging apparatus, such as, for example, possible degrees of freedom of movement, possible arrangements and/or dimensions of parts and/or components, in order to determine the application-appropriate position suitable for the target region 9 of the patient 15. As described above, the determination of the application-appropriate position can equally take place by the use of intelligent algorithms, such as, for example, self-learning algorithms, expert systems, neural networks or the like. Herein, it is conceivable that the intelligent algorithms process patient information, diagnostic data from the RIS and/or HIS, data from the body model, data from the imaging apparatus, data from the imaging-relevant component and data from databases with medical information.

In a further step S4, the positioning instruction is determined in dependence on the position of the patient 15 relative to the imaging-relevant component and the application-appropriate position of the imaging-relevant component. As described in step S3, the computing unit 40 can at least access information on the possible degrees of freedom of movement and the possible arrangement and dimensions of the imaging-relevant component. From this information, the computing unit 40 can determine a possible alignment and/or positioning of the imaging-relevant component and a movement trajectory. Herein, the alignment and the movement trajectory can, for example, be transformed into three-dimensional coordinates in order to generate the positioning instruction.

The current position of the imaging-relevant component relative to the target region of the patient 15 can be taken into account in the determination of the positioning instruction. In one example, the imaging-relevant component can be an X-ray source 7 whose distance and/or orientation with respect to the target region 9 of the patient 15 is acquired via one or more sensors 63 continuously or at discrete time intervals. However, it is equally conceivable that the imaging-relevant component is a patient table 17 whose distance or alignment with respect to the patient 15 remains almost unchanged when the patient table 17 is moved. In this case, for the determination of the positioning instruction, the current position of the patient table 17 relative to the imaging apparatus is preferably acquired via an incremental encoder 63c and taken into account in the determination of the positioning instruction. The determination of the positioning instruction in dependence on the data from one or more sensors 63 enables the positioning instruction to be adapted continuously or updated at discrete time intervals to the movement of the imaging-relevant component by the attending medical professional 29.

In a further step S5, the positioning instruction is output. The positioning instruction can, for example, be output as an optical, haptic or acoustic signal. The positioning instruction is preferably transferred via the output interface 43 to a display unit 41 in order to enable an attending medical professional 29 to transfer the imaging-relevant component into the application-appropriate position. The positioning instruction can in particular comprise a two-dimensional or three-dimensional map of part of the examination room in which the application-appropriate position of the imaging-relevant component is depicted schematically. Herein, the coordinates and/or location information in the positioning instruction can be registered in the three-dimensional map of the examination room or displayed as an object. This can mean that the movement trajectory of the imaging-relevant component is depicted in the three-dimensional map of the examination room. However, it is equally conceivable that only the application-appropriate position of the imaging-relevant component is mapped, for example in the form of a semi-transparent schematic drawing, as a positioning instruction in the three-dimensional map of the examination room. It is furthermore conceivable that the positioning instruction is transmitted in the form of acoustic tones, a voice instruction or haptic feedback, such as, for example, vibration, to the attending medical professional 29.

In one possible embodiment, the positioning instruction also comprises control signals embodied to actuate the motor element 61 and/or the braking apparatus 62. The control signals can, for example, be transmitted from the control unit 4 or the output interface 43 to the motor element 61 and/or the braking apparatus 62.

The positioning instruction is output continuously or at discrete time intervals. When the map of the examination room is output on the display unit 41, the positioning instruction can, for example, be output more frequently than 24 times a second, more frequently than 10 times a second, more frequently than 5 times a second, but also at a rate of one second or any multiple of one second. On the other hand, acoustic and/or haptic signals can also be output at a significantly higher frequency.

In a further step S6, the imaging-relevant component is positioned in the application-appropriate position in dependence on the positioning instruction. Herein, the in imaging-relevant component is preferably positioned manually, i.e. by the attending medical professional 29 or another user 29 of the imaging apparatus. The imaging-relevant component can be moved into the application-appropriate position by way of force exerted by the user 29, such as, for example, depressing, pushing, cranking, lifting, pressing or the like. Herein, the force applied by the user 29 is preferably coordinated with the positioning instruction, which is output to the user 29 continuously or updated at discrete time intervals on a display unit 41 to the user 29. Hence, the user 29 is able to coordinate the progress of the positioning of the imaging-relevant component with the positioning instruction.

In one embodiment, the imaging apparatus has a braking apparatus 62, which locks the imaging-relevant component in the application-appropriate position. This, for example, enables the user 29 to move the imaging component along a movement trajectory specified by the positioning instruction without having to pay attention to the actual achievement of the application-appropriate position. Herein, the imaging-relevant component is stopped or locked in the application-appropriate position via the braking apparatus 62 in dependence on a control signal of the positioning instruction. The braking apparatus 62 preferably has brake pads embodied to modulate a braking action of the braking apparatus 62. This enables the speed of the imaging-relevant component to be gently reduced during movement by the user 29 before the imaging-relevant component is locked in the application-appropriate position by transferring the braking apparatus 62 into the locking position.

In a further embodiment, the imaging apparatus can have a motor element 61 embodied to correct minor positioning errors of the imaging-relevant component. Such positioning errors can, for example, result from inaccurate positioning of the imaging-relevant component by the user 29. However, it is equally conceivable that the braking apparatus 62 has failed to lock the imaging-relevant component in the application-appropriate position as the result of the discontinuous or dynamic exertion of force by the user 29. The computing unit 40 can ascertain this incorrect positioning via the sensors 63 and issue a control instruction to the motor element 61 in order to transfer the imaging-relevant component into the application-appropriate position. The motor element 61 is preferably undersized with respect to the maximum possible deflection of the imaging-relevant component along a degree of freedom of movement. This can mean that the motor element 61 only moves and/or transports the imaging-relevant component along a limited path distance in order to correct minor positioning errors.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for positioning an imaging-relevant component of an imaging apparatus in an application-appropriate position for recording medical image data from a target region of a patient, the imaging-relevant component of the imaging apparatus being movable relative to at least one of a static arrangement of the imaging apparatus or the patient such that imaging is coordinated with the target region of the patient, the method comprising:
   acquiring information of the target region of the patient;
   acquiring a position of the patient relative to the imaging-relevant component;
   determining an application-appropriate position of the imaging-relevant component based on the information of the target region of the patient;
   determining a positioning instruction based on the position of the patient relative to the imaging-relevant component; and the application-appropriate position of the imaging-relevant component;
   outputting the positioning instruction, the outputting of the positioning instruction including outputting a control signal; and
   positioning the imaging-relevant component in the application-appropriate position based on the positioning instruction, wherein
      the positioning of the imaging-relevant component in the application-appropriate position is performed manually by a user, and
      during the positioning of the imaging-relevant component, the imaging-relevant component is locked in the application-appropriate position via a braking apparatus, the braking apparatus being transferred to a locking position based on the control signal.

2. The method of claim 1, wherein the determining of the application-appropriate position of the imaging-relevant component is performed via at least one of intelligent algorithms or a body model.

3. The method of claim 2, wherein the outputting of the positioning instruction includes outputting at least one of an optical signal, an acoustic signal or force feedback.

4. The method of claim 2, wherein the positioning of the imaging-relevant component in the application-appropriate position based on the positioning instruction includes,
   adjusting the position of the imaging-relevant component via a motor element to correct a positioning error during the positioning of the imaging-relevant component in the application-appropriate position, the motor element moving the imaging-relevant component into the application-appropriate position on the patient based on the positioning instruction.

5. The method of claim 1, wherein the outputting of the positioning instruction includes outputting at least one of an optical signal, an acoustic signal or force feedback.

6. The method of claim 1, wherein the positioning of the imaging-relevant component in the application-appropriate position based on the positioning instruction includes,
   adjusting the position of the imaging-relevant component via a motor element to correct a positioning error during the positioning of the imaging-relevant component in the application-appropriate position, the motor element moving the imaging-relevant component into the application-appropriate position on the patient based on the positioning instruction.

7. A non-transitory computer program product, loadable into a memory of a computing device of an imaging apparatus, the non-transitory computer program product storing program code for executing the method of claim 1 upon the program code being executed in the computing device of the imaging apparatus.

8. The method of claim 1, further comprising:
   transferring the braking apparatus to the locking position based on the control signal upon the imaging-relevant component being manually positioned by the user in the application-appropriate position.

9. The method of claim 1, wherein the positioning of the imaging-relevant component in the application-appropriate position is performed manually by the user via the application of manual force by the user.

10. An imaging apparatus, comprising:
    an imaging-relevant component including a mechanical guide configured to enable manual positioning of the imaging-relevant component along at least one degree of freedom of movement relative to at least one of a static arrangement of the imaging apparatus or a patient;
    at least one sensor configured to acquire a position of a target region of the patient relative to the imaging-relevant component;
    at least one processor configured to determine an application-appropriate position of the imaging-relevant component and to derive a positioning instruction based on the position of the patient relative to the imaging-relevant component; end an output interface configured to output the positioning instruction and a control signal; and a braking apparatus configured to lock the imaging-relevant component in the application-appropriate position based on the control signal.

11. The imaging apparatus of claim 10, wherein the at least one sensor is configured to acquire a position of the imaging-relevant component relative to the imaging apparatus, and the at least one processor is configured to determine the positioning instruction based on the position of the imaging-relevant component relative to the imaging apparatus.

12. The imaging apparatus of claim 11, a wherein the braking apparatus is configured to limit the at least one degree of freedom of movement of the imaging-relevant component at a position determined based on the positioning instruction.

13. The imaging apparatus of claim 11, wherein the imaging-relevant component of the imaging apparatus includes a motor element; configured to correct a positioning error of the imaging-relevant component based on the positioning instruction and to move the imaging-relevant component into the application-appropriate position along the at least one degree of freedom of movement.

14. The imaging apparatus of claim 10, wherein the apparatus is configured to limit the at least one degree of freedom of movement of the imaging-relevant component at a position determined based on the positioning instruction.

15. The imaging apparatus of claim 10, wherein the imaging-relevant component of the imaging apparatus includes a motor element-configured to correct a positioning error of the imaging-relevant component based on the positioning instruction and to move the imaging-relevant component into the application-appropriate position along the at least one degree of freedom of movement.

16. The imaging apparatus of claim 10, further comprising:

a display including a signal connection to the output interface, the display configured to output the positioning instruction to a user of the imaging apparatus.

17. The imaging apparatus of claim 16, wherein the display has a shape corresponding to a body region of the user of the imaging apparatus, the display is configured to be fastened to the body region of the user of the imaging apparatus, and the display is configured to output the positioning instruction as at least one of an optical signal, an acoustic signal, or force feedback to the user of the imaging apparatus.

* * * * *